United States Patent [19]

Russo

[11] 4,086,918
[45] May 2, 1978

[54] INHALATION DEVICE
[75] Inventor: Ronald D. Russo, Hamden, Conn.
[73] Assignee: Chesebrough-Pond's Inc., Greenwich, Conn.
[21] Appl. No.: 657,241
[22] Filed: Feb. 11, 1976
[51] Int. Cl.$^2$ ............................................. A63B 23/00
[52] U.S. Cl. .................................... 128/2.08; 272/99
[58] Field of Search ............. 128/2.08, 2.05 V, 142 R, 128/185, 202, 205, 145.8, 25; 272/99; 73/419, 209; 116/117 B, 117 C, 117 R

[56] References Cited
U.S. PATENT DOCUMENTS

| | | | |
|---|---|---|---|
| 393,869 | 12/1888 | Warren | 128/201 |
| 515,637 | 2/1894 | Wilhide | 272/99 R |
| 714,141 | 11/1902 | Cady | 128/2.08 |
| 793,177 | 6/1905 | Cady | 128/2.08 |
| 892,432 | 7/1908 | Judson | 272/27 |
| 1,926,748 | 9/1933 | Mackenzie et al. | 128/2.05 R |
| 2,100,898 | 11/1937 | Bernett | 273/95 |
| 3,087,278 | 4/1963 | Waggle, Jr. | 46/44 |
| 3,633,421 | 1/1972 | Phillips | 73/209 |
| 3,695,608 | 10/1972 | Hanson | 128/2.08 |
| 3,754,546 | 8/1973 | Cooper | 272/99 |
| 3,898,987 | 8/1975 | Elam | 128/145.8 |

FOREIGN PATENT DOCUMENTS 8,662 of 1903 United Kingdom ................... 272/99

Primary Examiner—Kyle L. Howell
Assistant Examiner—Henry J. Recla
Attorney, Agent, or Firm—Morgan, Finnegan, Pine, Foley & Lee

[57] ABSTRACT

An inhalation device which induces respiratory exercise and which is inexpensive, safe and easy to handle and operate. The device includes a flow measurement container in which is housed a flow rate indicator, such as a light-weight article or ball, that normally rests at the bottom of the container. Extending through the top wall are opposed ports. A restricted port connects the chamber to atmosphere and a large opposing port to a passageway through which a person inhales. With the inhalation device of the invention, the user, nurse, or therapist can readily measure the amount inspired. A predetermined amount of inhalation for a given time is required to raise the indicator to the top of the container and predetermined additional amounts of inhalation for a given additional times are required to maintain the article at the top thereof.

15 Claims, 9 Drawing Figures

INHALATION DEVICE

FIELD OF THE INVENTION

The present invention relates to an inhalation device for inducing a person to expand and use his or her lungs and respiratory musculature.

BACKGROUND OF THE INVENTION

It is often necessary to induce patients to expand and use their lungs and respiratory musculature. Post-surgical, bed-ridden, inactive, obese and geriatric patients do not utilize their respiratory systems fully. Pain, illness and feebleness inhibit use. As a consequence, these people are prone to pulmonary complications such as lung congestion and hypostatic pneumonia. The inefficient use of the respiratory system also can retard healing and cause muscle atrophy.

Thus, a need exists to provide patients with an incentive which encourages use of their respiratory systems. In general, presently available apparatus for inducing said use by inhalation is relatively expensive and awkward to handle. Further, the apparatus is comparatively costly and complex, and is generally limited to hospital use because of the complexities and costs. In addition, presently available apparatus is made up of a multiplicity of parts which, when dropped, are susceptible to breakage and which are costly to replace.

It is an object of this invention, therefore, to provide a new and improved device which induces respiratory exercises through inhalation without drawbacks of presently available devices and systems.

Among the other objects of this invention is to provide an inhalation device which provides the requisite incentive and encourages use by ease of handling and operation; to provide an inhalation device which is safe to use; to provide an inhalation device, the successful use of which easily can be seen and measured by the patient, nurse or others; and to provide an inhalation device which accomplishes the foregoing while being relatively inexpensive.

Additional objects and advantages will be set forth in part hereinafter and in part will be obvious herefrom or may be learned with the practice of the invention, the same being realized and obtained by means of this respiratory stimulator recited in the appended claims.

SUMMARY OF THE INVENTION

In accordance with the invention there is provided an incentive inhalation device, comprising a flow measurement container. In its upright position the container has a top wall, a bottom wall and a see-through vertical wall. Extending from the top and bottom wall within the container is a chamber in which a flow rate indicator, such as a light-weight article or ball, normally rests at the bottom thereof. A clearance fit is provided between the indicator and chamber wall which allows for free vertical movement of the indicator but restricts air flow about the indicator for causing it to rise when a precalibrated inhalation effort is achieved. Extending through the top wall are opposed ports. A restricted air intake port connects the chamber to the surrounding atmosphere and an opposing larger port connects the chamber to an air inhalation passageway which extends alongside the container and is connected to an air outlet.

Preferably, the container is positioned on a base which makes the device self-supporting in the vertical position, and the inhalation passageway extends from an outlet in the front of the base and under the container and upwardly in a vertical channel.

Connected to the outlet of the passageway are means, such as flexible tubing and a mouthpiece, which allow a person to withdraw air from the container chamber upon inhaling.

In use, a person places his or her mouth over the mouthpiece and inhales. This causes air to be withdrawn from the top of the chamber. The flow is across the chamber from the restricted port to the larger port and down through the passageway. As the person continues to inhale, a venturi effect created by the restricted port causes a pressure differential within the chamber with the air pressure at the top of the chamber being less than the air pressure at the bottom chamber. At the same time a lifting air stream is created by the air rushing into the chamber through the restricted port and through the clearance between the flow indicator and the chamber wall. Air flows down and about the indicator, hits the bottom wall and falls upwardly against the indicator. When a precalibrated inhalation effort is achieved within a predetermined time the pressure differential and the lifting air stream will cause the indicator to move to the top of the container and be maintained there until the person's efforts drop below the desired flow rate.

The device of the invention is particularly useful for inducing and measuring sustained inspiration which meets at least a desired minimum inhalation effort. For example, a precalibrated amount of inhalation for a predetermined time is required to raise the article to the top of the chamber, and precalibrated additional amounts of inhalation within additional predetermined additional times are required to maintain the indicator at the top of the chamber. In the preferred embodiment illustrated in the drawings and described hereinafter, at least 750 cubic centimeters per second must be inspired by the user to raise and maintain the ball to the top of the container. Accordingly, to maintain the ball at the container top for two seconds, at least 1500 cubic centimeters must be inspired within that time, and to maintain the ball at the top for four seconds, at least 3000 cubic centimeters must be inspired during this interval.

The device of the present invention therefore provides incentive levels of achievement for the patient which are designed to correspond to proper use of the respiratory system and to help restore and maintain lung capacity and musculatory strength.

Furthermore, with the outlet at the bottom and front of the device and with the passageway under and long the back of the container, the user can easily see the ball and measure his or her efforts.

Also, in accordance with the invention, means are provided within the chamber to prevent the indicator from actually contacting the bottom or top walls within the chamber to facilitate moving of the indicator upward and to prevent the indicator from closing the port and surprising the user through the disruption of air flow.

In construction, the device is compact and safe. Within the inhalation passageway there is provided a filter which prevents loose particles picked up in the air flow from exiting and being inhaled by the user. In addition, where the device is made of several plastic components, they are placed together and are preferably ultrasonically welded into a single integral break resistant unit. This obviates the need of deleterious materials, such as glue, which are known to give off residual vapors over a long period of time.

Moreover, by tilting the device, e.g., rearwardly, the force needed to overcome the force of gravity in the indicator is lessened so that the indicator can be raised to the top of the container more easily. Particularly ill or feeble patients are thereby provided with an incentive level they can achieve, and, in so doing, obtain needed respiratory exercise. To be able to accurately measure the flow rate when the container is tilted, means, such as a platform, are provided which can maintain the container at the desired angle. In the embodiment hereinafter described and illustrated in the drawings, the platform is provided with means for maintaining the container at several predetermined angles. For example, when the container is tilted rearwardly some 85°, an inhalation rate of only 250 cubic centimeters per second is required to raise and maintain the ball at the top of the container.

In addition, a dispenser, such as a nebulizer, can be placed at the outlet end of the device for inhalation of medicine upon inspiration by the patient.

BRIEF DESCRIPTION OF THE DRAWINGS

The following is a detailed description together with accompanying drawings of a preferred embodiment of the invention. It is to be understood that the invention is capable of modification and variation apparent to those skilled in the art within the spirit and scope of the invention.

In the drawings.

Figure 1:
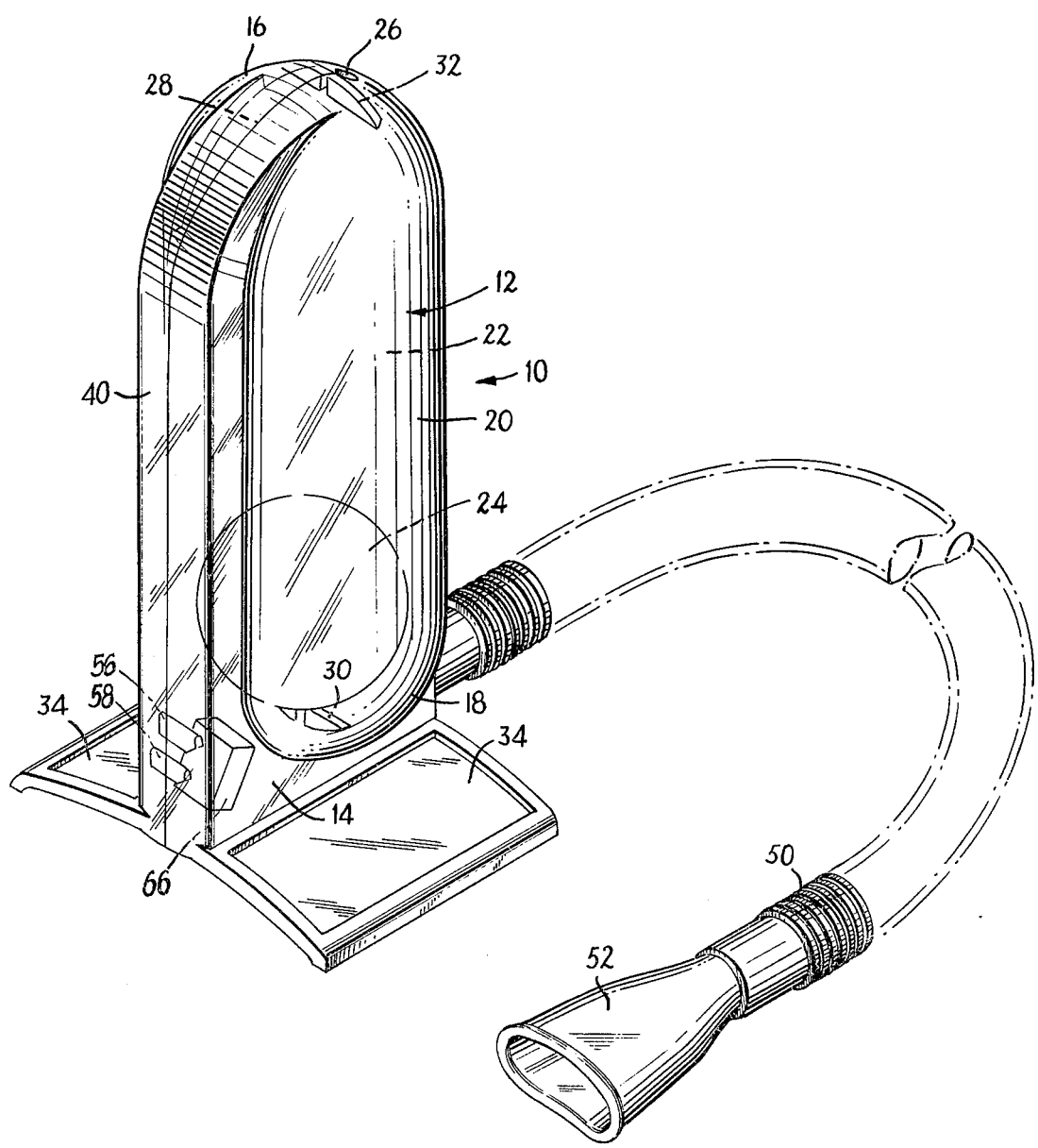
FIG. 1 is a perspective view of an inhalation device constructed in accordance with the present invention.

Referring to the drawings, the inspirator 10 is a transparent integral unit which includes a flow measurement container 12, mounted on a base 14.

The container 12 has a hemispherically or dome shaped top 16 and bottom 18 with a cylindrically shaped intermediate wall 20 which defines a chamber 22 for a light-weight indicator 24, such as a small colored plastic ball.

Extending through the top 16 are two ports 26 and 28. The port 26 extends through the front portion of the top 16 and connects the chamber 22 with the surrounding atmosphere. The port 26 is circular in cross-section and is restricted in breadth to provide a venturi effect with the chamber 22. The port 28 extends through the back portion of the top 16 and connects the chamber 22 with air passageway hereinafter described in detail. The port 28 is rectangular in cross-section and has a breadth substantially larger than the breadth of the restricted port 26. As shown, the bottom 18 does not include any openings or perforations.

The relative diameter of the ball 24 to the inner diameter of the wall 29 allows free movement of the ball 24 within the chamber 22 while restricting air flow about the ball. If the gap or clearance between the ball 24 and wall 20 is too small, the ball 24 may become stuck in the chamber 24. If the gap is too large, the desired inhalation effort will not effect pressure differentials and air streams within the chamber 22 necessary to lift the ball 24. In the illustrated embodiment a total clearance fit or gap between the wall 29 and ball 24 of about 0.125 inches to 0.25 inches is provided.

Similarly, the relative sizes of the ports 26 and 28 are such that they provide the requisite incoming air stream through port 26 when the desired inhalation is achieved. In this device exhalation or blowing into the chamber 22 does not cause the ball 24 to rise at all. Instead, the inner surfaces of the top 16 and wall 20 become clouded because of condensation. In the illustrated embodiment the port 26 has a diameter of about 0.187 inches providing an opening having an area of 0.008 square inches and the port 28 has a height of about 0.25 inches and a width of about 0.50 inches providing an opening having an area of 0.125 square inches. In other words, port 28 has an area which is about sixteen times that of port 26.

In general, upon inhalation air is removed from the top of the chamber 22 through port 28 causing atmospheric air to rush into the chamber 22 through port 26. A portion of such air will move across the top chamber 22 and into the passageway through port 28 and a portion will move downwardly around the ball 24 and be redirected upwardly against the ball 24 by the bottom 18. This flow creates a lifting air stream and a pressure differential in the chamber 22 with the air pressure at the top of the chamber being less than at the bottom, all of which causes the ball 24 to rise. To facilitate the rise of the ball 24 and to prevent the ball 24 from closing port 26, ridges 30 and 32 are provided within the container 12. The lower ridge 30 extends upwardly and prevents the ball from contacting the bottom of the container. The upper ridge 32 depends downwardly adjacent to the port 26 to prevent closing the port 26 by the rising ball 24 which would disrupt the desired flow of air and cause surprise or shock to the user.

The base 14 on which the container bottom 18 is positioned, includes a pair of arms 34 which extend laterally from the two sides of the base 14 outwardly and downwardly to serve as a stand for the inspirator so that it will stand by itself in an upright or vertical position.

Extending vertically upwardly from the base 14 and continuous with the container rear wall 38 is a vertical shaped channel 40 which terminates at its upper end in a tapered segment 42 that is inwardly curved to compliment the dome shaped top 16.

Extending through the base 14 and channel 40 and container rear wall 38 is an "L" shaped air passageway 44. The horizontal section 46 of the passageway 44 is centrally positioned and extends directly under the container bottom 18, and terminates at its outer or front end in an outwardly extending integral tube 48. Slidably fitted over the outlet tube 48 is a flexible accordian tubing 50 which has at its outer end a mouthpiece 52 slidably fitted thereinto.

The vertical section 54 of the passageway 44 extends from the inner or back end of the horizontal section 46 vertically upward to the port 28. At the juncture of the vertical and horizontal sections of the passageway 44 there is provided two vertically spaced and two horizontally spaced tabs 56, 58, 60 and 62, respectively. The inner vertical tab 56 is placed above vertical tab 58 and inner horizontal tab 60 is placed in front of tab 62 to define a slot 64 which is at an acute angle with the horizontal section 46 of the passageway 44. Extending across the passageway 44 and force fitted within the angular slot 64 is a rectangularly shaped filter 66 which captures loose particles that may pass through port 26 and into passageway 44.

Figure 2:
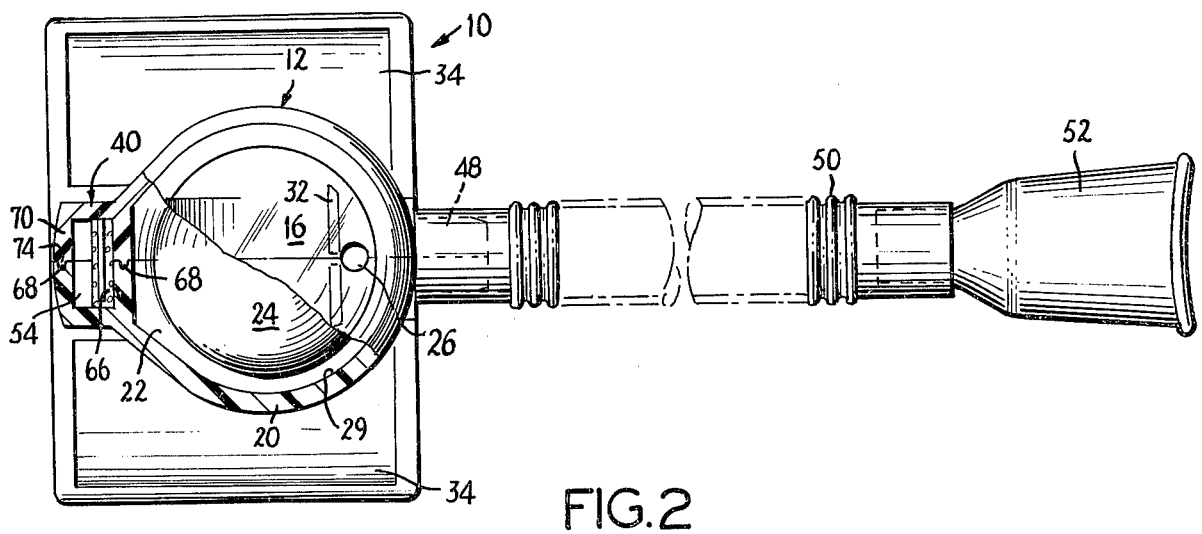
FIG. 2 is a plan view of the device illustrated in FIG. 1 with the top of the container and vertical channel away to show details of construction.
Figure 3:
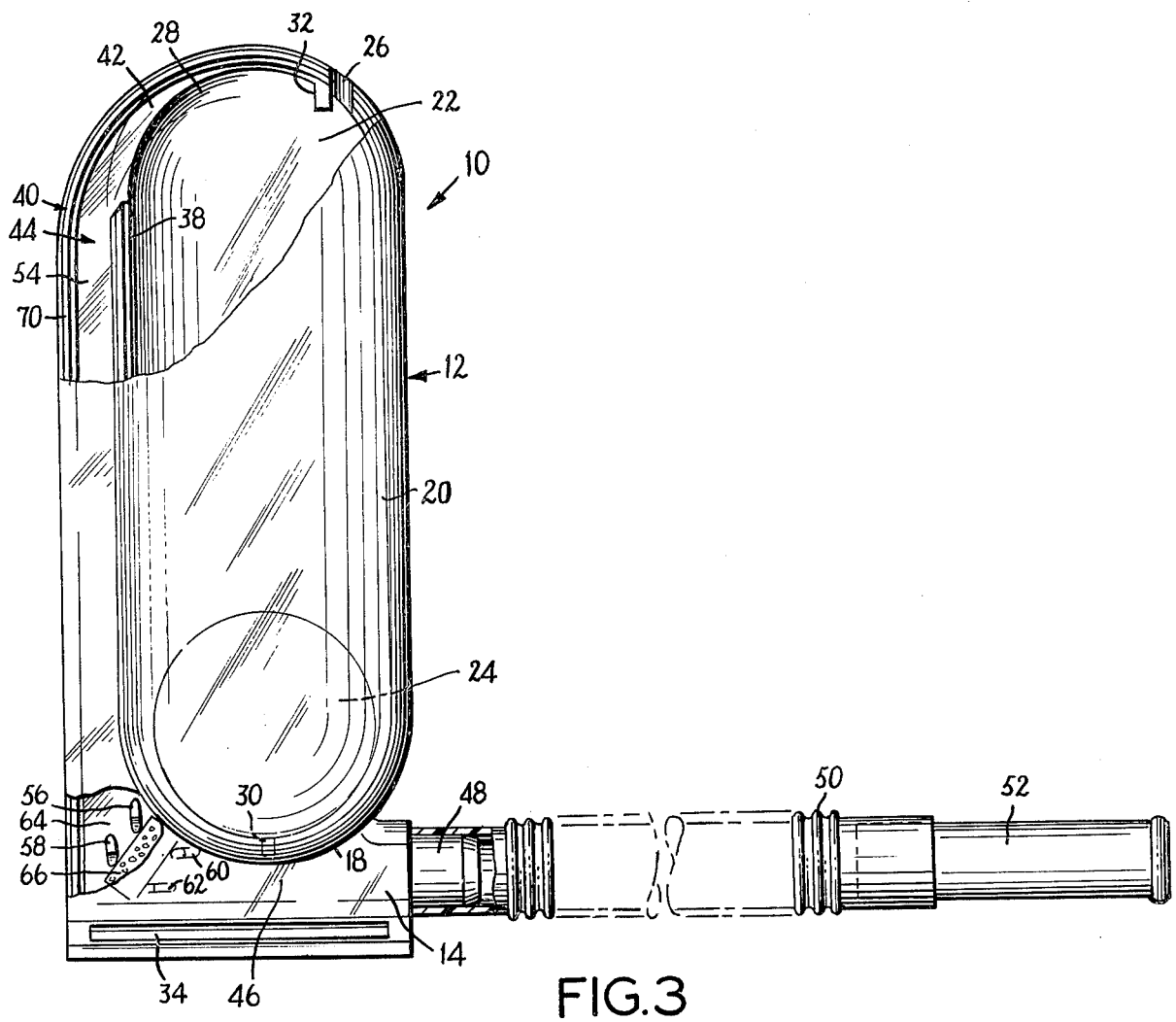
FIG. 3 is a side view of the device illustrated in FIG. 1 in which the container and vertical channel are partially broken away to show details in construction.
Figure 4:
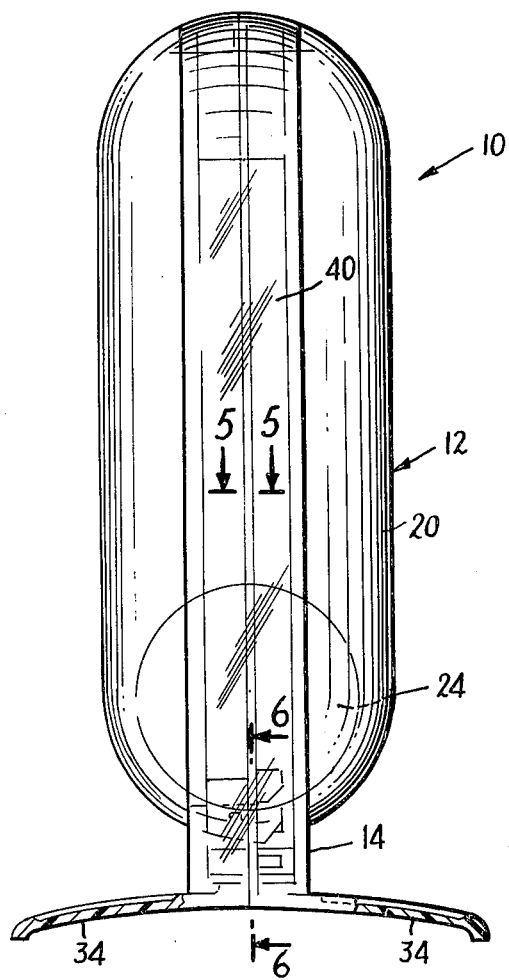
FIG. 4 is an end view looking at the back of the device illustrated in FIG. 1.
Figure 5:
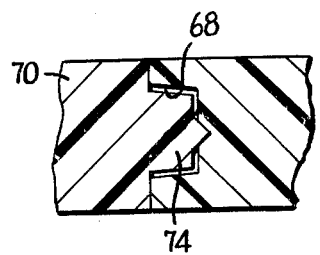
FIG. 5 is a sectional view of FIG. 4, taken along the lines 5—5, illustrating the tongue and groove construction of the mating parts.
Figure 6:
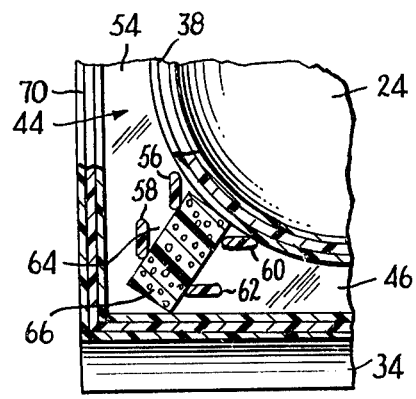
FIG. 6 is a sectional view of FIG. 4, taken along the lines 6—6, showing the filter in the air passageway which prevents loose particles from being inhalated.

In the preferred embodiment illustrated in the drawings, the inspirator 10 is formed in a two part conventional injection mold. Each part is a vertical section of the inspirator, which, as illustrated in FIG. 2, is one-half of the assembled inspirator taken along a center line which cuts across the channel 40 and container 12. Also, as illustrated in FIGS. 2 and 5, the face of the lower or right hand section is formed with grooves 68 in the container inner wall 38 and channel outer wall 70. Correspondingly, the upper or left hand section is formed with tongues 74 in the container inner wall 38 and the channel outer wall 70 which slidably fit into the grooves 68.

In assembling the illustrated inspirator, the filter 66 is inserted in the slot 64, a ball 24 is placed in one section of the container 12 and the molded sections are brought together so as to cause the tongues 74 to fit into the grooves 68. With the inspirator 10 assembled, the sections are ultrasonically welded together to form a single integral device 10. In so doing, the need for glue, the deleterious vapors of which remain long after use, is obviated.

In operation, the patient or user places his or her mouth over the mouthpiece 52 and inhales. This action causes air to be withdrawn from the top of the container 12 and creates a pressure differential in the chamber 22, wherein the pressure in the lower portion of the chamber 22 is higher than the pressure in the upper part of the chamber 22. At the same time, inrushing air flow downwardly about the ball 24 and is reflected upwardly by the bottom 18 against the ball 24. When the pressure differential and lifting air stream reach a predetermined level that corresponds to the desired inhalation rate, the ball 24 within the chamber 22 will begin to rise. Continued inhalation at the predetermined rate will cause the ball 24 to rise to the top of the chamber 22 and contact ridge 32 where it will remain as long as the user continues to withdraw sufficient air from the top of the chamber 22 at that rate.

The device of the present invention therefore measures the minimum flow rate of inspiration needed to lift and maintain ball 24 of the container top 16. In the device illustrated in the drawings, the ball 24 is about 1.50 inches in diameter and weighs 2.5 grams. The ball 24 will move to the top of the chamber 22, which is about 5.5 inches in length and 1.75 inches in cross section, when the inhalation flow rate from the chamber 22 is at least about 750 cubic centimeters per second. To thereafter maintain the ball 24 in the suspended state, a flow rate of at least about 750 cubic centimeters must be maintained. From this flow rate total volume inspired is easily calculated, e.g., at least 1500 cubic centimeters for two seconds; at least 3000 cubic centimeters for four seconds; at least 4500 cubic centimeters for six seconds. Thus, a patient, nurse, and others can tell that at least so many cubic centimeters have been inspired by timing how long the ball 24 remains suspended. As a reminder, the foregoing information may be imprinted directly on an arm 34 or on a label affixed to an arm 34.

The action of the ball 24 also is readily seen because the air passageway 44 is under and along the back of the container 12 giving the user a clear unimpeded view.

Further, the device of the invention is compact and easy to handle. The illustrated device stands some six inches high and is about six inches in length and is about three inches wide. Patients therefore can easily handle and operate the device. Flexible tubing 50 of some 11.0 inches has been found convenient.

In the illustrated embodiment, moreover, the filter is made from urethane foam of about 0.57 inches in length and 0.25 inches in thickness. The illustrated filter has 10 pores per inch to present a tortuous path for the air flow to prevent loose particles from passing therethrough.

The device 10 of the invention is preferably formed from plastics which are inert and stable in the formed device 10 and which lend themselves to processing by plastic forming techniques, and will, when formed, provide the break resistant, see-through self-supporting device described and claimed herein. In the preferred embodiment the see-through device is formed by injection molding polystyrene. Other materials and plastics which provide the desired see-through properties also can be used, including styrene-acrylonitrile copolymers, rigid polyvinylchloride polymers and poly carbonate polymers.

Moreover, the flow rate of 750 cubic centimeters per second for the device 10 illustrated in the drawings corresponds to the mid-range of a deep breath. It is within the scope of this invention to provide devices 10 with different flow rates which can be made to correspond to the condition of the patient. For example, by further restricting the port 26 a flow rate which corresponds to a full deep breath, e.g., 1000 cubic centimeters per second, is provided. This device can be used for a patient who is near full recovery. Correspondingly, by enlarging the port 26 a flow rate which corresponds to lower range of a deep breath, e.g., 500 cubic centimeters per second, is provided. This device can be used for a feeble or seriously ill patient.

Figure 7:
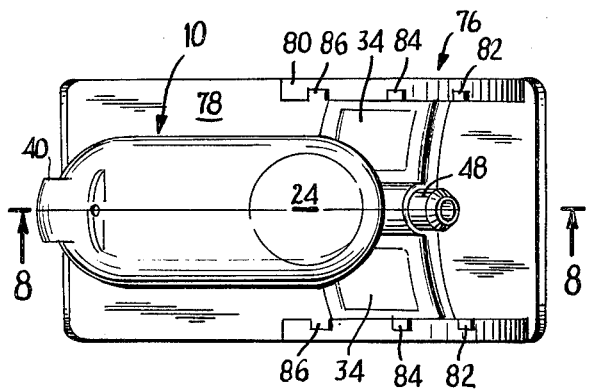
FIG. 7 is a plan view of the platform for maintaining the device in a rearwardly tilted position to reduce the inhalation effort needed to raise and maintain the ball at the top of the container.
Figure 8:
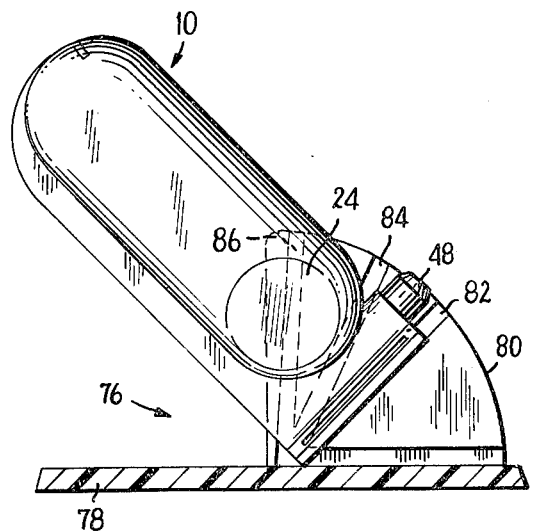
FIG. 8 is a side view with the foreground side wall removed to more clearly show the grooves into which the base of the device is slidable.

In addition, the device 10 can be tilted to reduce the inhalation effort needed to raise and maintain the ball 24 at the top of the container 10. In the device 10 shown in the drawings by tilting the device 10 rearwardly, the lifting force needed to overcome the force of gravity is reduced. The greater the tilt the less the inhalation effort needed to achieve lifting and maintaining the ball at the top of the container 12. In tilting the device 10, however, it becomes more difficult to measure flow rate when the angle of tilt cannot be ascertained. To overcome this difficulty, the present invention includes, as shown in FIGS. 7 and 8, a platform 76 having a self-standing base 78 and two side walls 80. Included in each side wall are grooves 82, 84 and 86 which are set at 45°, 65° and 85° to the base 76. In use, base 14 of the container 12 is slidable into opposing grooves so that any one readily can tell the angle of the tilt.

The device 10 illustrated in the drawings is precalibrated to provide a flow rate of 650 cubic centimeters per second at 45°; 550 cubic centimeters per second at 65°; and 250 cubic centimeters per second at 85°.

Thus, regardless of the condition of the patient, the present invention provides an incentive for a patient to use his or her lungs and chest. As that patient recovers, the angle of the tilt can be reduced until the device is vertically upright. In this way, the patient realizes his or her improvement.

Figure 9:
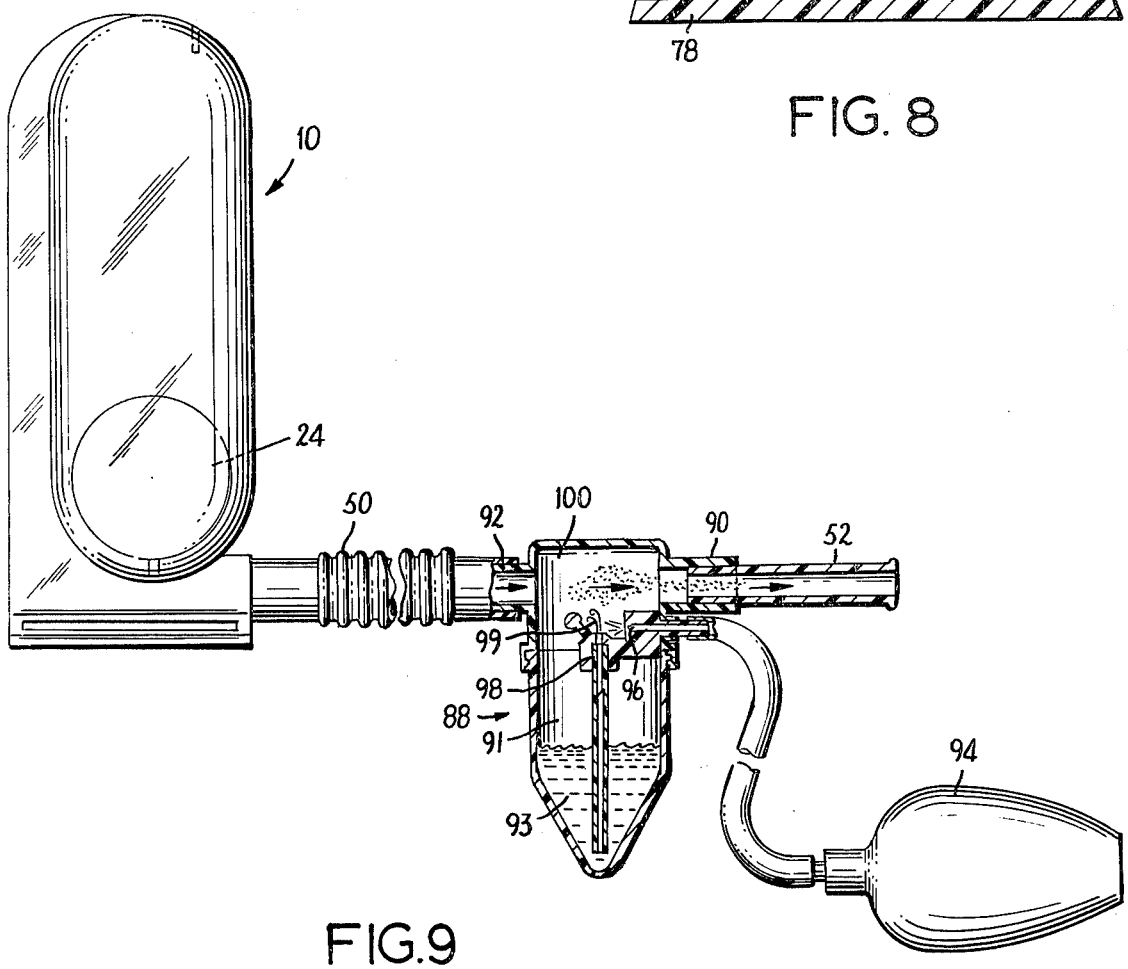
FIG. 9 is a side view, partly broken away, to show the dispenser for dispensing medicine through the flexible tubing upon inhalation.

Also, the present invention as shown in FIG. 9, includes a medicinal dispenser 88 connected at one end 90 to the mouthpiece 52 and at the other end 92 to the flexible tubing 50. Upon inhalation the patient will inspire the medicine in spray or powder form as he or she exercises his or her lungs and musculature. The medicinal dispenser 88 of the invention can be used to dispense bronchial dilators, water vapor, anti-inflammatory agents and asthmatic and other medicines. As shown the reservoir 90 is filled with medication 93 usually around 5 cc. The patient inhales trying to raise the ball 24. While inhaling, he squeezes on the bulb 94. Air from the bulb is forced through the nozzle 96 and across the tip of the tube 98. This rapidly-forced air creates an upward venturi suction in the tube 98 thus lifting up medication from the reservoir 90. As medication squirts out the tube 98, the rapidly-forced air breaks up the liquid into an aerosol mist. The aerosol is further atomized by the diffuser 99 into smaller particles. Atomized medication is now in the upper mist chamber 100. Inhaled patient air rushes across the mist chamber 100 thus carrying the atomized medication into the respiratory system of the patient. Large, unwanted particles fall back down into the reservoir 90. Only the desired small 0.5 micron to 6 micron particles are inhaled to reach deep into the lungs. The amount of medication delivered is controlled by viewing through the reservoir 90.

The invention in its broader aspect is not limited to the specific described embodiments and departures may be made therefrom within the scope of the accompanying claims without departing from the principals of the invention and without sacrificing its chief advantages.

What is claimed is:

1. A self-supporting incentive inhalation device for inducing respiratory exercises comprising:

a container having a front and back portion, a top wall and a non-perforated bottom wall and an intermediate see-through wall forming a chamber within said container which extends between said top and bottom walls, a light-weight article in said chamber normally at the bottom thereof, but which, upon inhalation by the user at a precalibrated flow rate, will rise towards the top thereof, opposing openings extending through the upper portion of said container and into said chamber wherein through one of said openings air flows from the chamber upon inhalation, and wherein the opposing opening connects the chamber to atmosphere which flows into and through the chamber and said one opening for lifting said article upon inhalation, an inhalation passageway integral with said device wherein said passageway extends from the front and bottom of said container and up along the back of said container and said passageway being formed by the surface of said walls adjacent said passageway and a channel integral therewith, and, where at its upper end, said passageway is connected to said one opening, and means connected to said passageway at the front and bottom of said container to allow a person to withdraw air from said chamber to cause a flow of air into the chamber through said opening connected to atmosphere through the chamber and into said opposing opening and passageway which causes said article therein to rise to and be maintained at the top of said chamber when the user reaches and maintains an inhalation effort which is at least at the precalibrated flow rate, said passageway and last said means leaving a clear view of said chamber within said container so that said article in said chamber easily can be seen and followed by the user.

2. A self-supporting incentive inhalation device for inducing respiratory exercise, comprising:

a container having a front and back portion, a top wall and a non-perforated bottom wall and a vertical see-through cylindrical wall therebetween forming a chamber which extends between said top and bottom wall, a light-weight article in said chamber normally at the bottom thereof which has a clearance with respect to said cylindrical wall to allow said article to rise and be maintained at the top of said container upon inhalation at a precalibrated flow rate, opposing ports extending through said top wall wherein one of said ports is restricted and connects said chamber with the surrounding atmosphere and through which air flows into and through said chamber for lifting the article upon inhalation, an inhalation passageway integral with said device connected to the opposing port which is larger than said restricted port, and wherein said passageway extends from an outlet at the bottom of said container, up along and integral with the back of said container where it connects into said larger port, said passageway being formed by the surface of said walls adjacent said passageway and a channel integral therewith, and means connected to said outlet to allow a person by inhalation to withdraw air from said chamber to thereby effect air flow into said chamber through said restricted port and air flow from said chamber through said larger port which creates a pressure differential in said chamber wherein the pressure at the top thereof is less than the pressure of its bottom, and a lifting stream of air to flow down, about, under and up against said article, all of which causes said article to rise to the top of the chamber and remain there as long as the inhalation effort is maintained at least at a precalibrated flow rate, said passageway and last said means leaving a clear view of the see-through container chamber so that said lightweight article in said chamber easily can be seen and followed by the user.

3. The device of claim 2 in which said device is precalibrated so that said indicator will rise to and be maintained at said container top at a predetermined flow rate of about 500 to 1000 cubic centimeters per second.

4. A self-supporting incentive inhalation device for inducing respiratory exercise, comprising:

a container having a front and back portion, a top wall and a non-perforated bottom wall and a vertical see-through cylindrical wall therebetween forming a chamber which extends between said top and bottom wall, a light-weight article in said chamber normally at the bottom thereof which has a clearance with respect to said cylindrical wall to allow said indicator to rise and be maintained at the top of said container upon inhalation at a precalibrated flow rate, a restricted port extending through the front portion of said top wall connecting said chamber to the surrounding atmosphere, a larger port in the back portion of said top wall open at its inner end to said chamber, an inhalation passageway integral with said device connected to said larger port, wherein said passageway extends from the front of the device under said container and then up along the back portion of and integral with said container where it connects into said larger port, said passageway being formed by the outer surface of said walls adjacent said passageway and a channel integral therewith, and means connected to said passageway at the front of and below said container to allow a person by inhalation to withdraw air from said chamber to thereby effect air flow into said chamber through said restricted port and air flow from said chamber through said larger port which creates a pressure differential in said chamber wherein the pressure at the top thereof is less than the pressure of its bottom, and a lifting stream of air flows down, about, under and up against said article, all of which causes said article to rise to the top of the chamber and remain there as long as the inhalation effort is maintained at the predetermined flow rate, said passageway and last said means leaving a clear front view of the see-through container cylinder so that said light-weight article in said chamber can be easily seen and followed by the user.

5. A self-supporting incentive inhalation device for inducing respiratory exercise comprising:

a container having a front and back portion, a top wall and a non-perforated bottom wall and an intermediate see-through wall forming a chamber within said container which extends between said top and bottom walls, a flow rate indicator in said chamber normally at the bottom thereof, but which, upon inhalation by the user at a precalibrated flow rate, will rise towards the top thereof, opposing openings extending through the upper portion of said container and into said chamber wherein one of said openings is connected to the upper portion of said chamber and through which air flows from the chamber upon inhalation, and wherein the opposing opening connects the chamber to atmosphere which flows into and through the chamber for lifting the indicator upon inhalation, an inhalation passageway integral with said device wherein said passageway extends from the front portion and bottom of said container and up along and integral with the back of said container where it is connected to said one opening, said passageway being formed by the surface of said walls adjacent said passageway and a channel integral therewith means connected to said passageway at the front and bottom of said container to allow a person to withdraw air from said chamber to cause a flow of air into the chamber through said opening connected to atmosphere through the chamber and into said opposing opening and passageway which causes the indicator therein to rise to and be maintained at the top of said chamber when the user reaches and maintains an inhalation effort which is at least at the precalibrated flow rate, said passageway and last said means leaving a clear view of said chamber within said container so that said flow indicator in said chamber easily can be seen and followed by the user, and means in said chamber for preventing said indicator from closing said openings in the upper portion of said chamber when it is at the top thereof, to thereby prevent a surprise or shock to the user by the disruption of air flow.

6. A self-supporting incentive inhalation device for inducing respiratory exercises comprising:

a container having a front and back portion, a top wall and a non-perforated bottom wall and an intermediate see-through wall forming a chamber within said container which extends between said top and bottom walls, a light-weight article in said chamber normally at the bottom thereof, but which, upon inhalation by the user at a precalibrated flow rate, will rise towards the top thereof, opposing openings extending through the upper portion of said container and into said chamber wherein through one of said openings air flows from the chamber upon inhalation, and wherein the opposing opening connects the chamber to atmosphere which flows into and through the chamber and said one opening for lifting said article upon inhalation, a base integral with the bottom of said container which extends outwardly to make said device self-supporting in an upright vertical position, an inhalation passageway integral with said device wherein said passageway extends from the front and bottom of said container through said base and up along the back of said container, said passageway extending along the back of said container being formed by the outer surface of said walls adjacent said passageway and a channel integral therewith, and, where at its upper end, said passageway is connected to said one opening, means connected to said passageway at the front and bottom of said container to allow a person to withdraw air from said chamber to cause a flow of air into the chamber through said opening connected to atmosphere through the chamber and into said opposing opening and passageway which causes said article therein to rise to and be maintained at the top of said chamber when the user reaches and maintains an inhalation effort which is at least at the precalibrated flow rate, said passageway and last said means leaving a clear view of said chamber within said container so that said article in said chamber easily can be seen and followed by the user, and means in said chamber for preventing said article from closing said openings in the upper portion of said chamber when it is at the top thereof, to thereby prevent a surprise or shock to the user by the disruption of air flow.

7. A self-supporting incentive inhalation device for inducing respiratory exercise, comprising:
- a container having a front and back portion, a top wall and a non-perforated bottom wall and a vertical see-through cylindrical wall therebetween forming a chamber which extends between said top and bottom wall,
- a light-weight article in said chamber normally at the bottom thereof which has a clearance with respect to said cylindrical wall to allow said indicator to rise and be maintained at the top of said container upon inhalation at a precalibrated flow rate,
- a restricted port extending through the front portion of said top wall connecting said chamber to the surrounding atmosphere,
- a larger port in the back portion of said top wall open at its inner end to said chamber,
- an inhalation passageway integral with said device connected to said larger port, wherein said passageway extends from the front portion and bottom of said container and then up along and integral with the back of said container where it connects into said larger port,
- a filter in said passageway for preventing the inhalation of solids,
- flexible tubing connected at one end to said passageway at the front of and below said container and a mouthpiece connected at the other end of said flexible tubing to allow a person by inhalation to withdraw air from said chamber to thereby effect air flow into said chamber through said restricted port and air flow from said chamber through said larger port which creates a pressure differential in said chamber wherein the pressure at the top thereof is less than the pressure of its bottom, and a lifting stream of air flows down, about, under and up against said article, all of which causes said article to rise to the top of the chamber and remain there as long as the inhalation effort is maintained at the predetermined flow rate,
- said passageway, tubing and mouthpiece leaving a clear front view of the see-through container cylinder so that said light-weight article in said chamber can be easily seen and followed by the user,
- a ridge extending upwardly from said bottom wall into said chamber to prevent said article from directly contacting said bottom wall so that lifting air can flow under and up, against said article, and
- a ridge depending from said top wall and extending into the top portion of said chamber which prevents said article from disrupting the flow of air through said chamber by closing at least one of said ports.

8. The inhalation device of claim 7, including a base extending outwardly from below said container which makes said device self-supporting in an upright vertical position and through which said passageway extends.

9. A self-supporting incentive inhalation device for inducing a person to expand and use his or her lungs, comprising:
- a transparent container having a hemispherically shaped top and bottom walls and cylindrical wall therebetween which forms a chamber in said container which extends from said bottom to said top walls,
- a ball in said chamber having a minimum clearance with said cylindrical wall which normally rests at the bottom thereof but which upon inhalation at a precalibrated flow rate selected from the range of about 500 to 1000 cubic centimeters per second will cause said ball to rise and be maintained at said container top,
- a restricted port extending through the front portion of said top wall connecting said chamber to the surrounding atmosphere,
- a larger port extending through the back portion of said top wall open at its inner end to said chamber,
- a ridge extending upwardly in said chamber from the bottom of said container to prevent said ball from directly contacting said container bottom,
- a ridge depending in said chamber from the top of said container adjacent to said atmospheric connecting port to prevent said ball from closing said port and disrupting air flow across the top of said chamber, and
- a base on which said container is positioned and from which said base laterally extends so that the device stands by itself in the vertical upright position,
- a closed vertical channel extending upwardly from said base along the back of said container to and over said back port,
- an inhalation passageway having an outlet below said container and in front of said device and extending horizontally through said base under said container vertically upward thorugh said channel where it is connected to said larger port, and
- flexible tubing connected to one end thereof to said passageway outlet and at the other end thereof to a mouthpiece to allow the user by inhalation to withdraw air from said chamber which at the selected flow rate will cause said ball to rise to and be maintained at said container top for as long as said flow rate is maintained.

10. The inhalation device of claim 9 which includes a filter in said passageway to prevent loose particles from exiting said passageway into said flexible tubing upon inhalation.

11. The inhalation device of claim 9 in which said preselected flow rate is about 750 cubic centimeters per second.

12. The inhalation device of claim 9 in which the device is made of polystyrene and is formed from a plurality of pieces ultrasonically welded together into a single, integral unit.

13. The inhalation device of claim 9 in which said device includes means for maintaining said container at a predetermined angle to reduce the flow rate necessary to cause said ball to rise and be maintained at the top of said container.

14. The inhalation device of claim 9 in which said device includes a platform into which said container is slidable at predetermined acute angles to reduce the flow rate necessary to cause said ball to rise and be maintained at the top of said container.

15. The inhalation device of claim 9 in which a medicinal dispenser is connected between said outlet and said tubing for dispensing medicine upon inhalation.

* * * * *

UNITED STATES PATENT OFFICE
CERTIFICATE OF CORRECTION

Patent No. 4,086,918        Dated May 2, 1978

Inventor(s) Ronald D. Russo

It is certified that error appears in the above-identified patent and that said Letters Patent are hereby corrected as shown below:

First page, line 8 of Abstract, Correct "large" to read --larger--.

Column 1, line 45, Change "this" to read --the--.

Column 2, line 20, Correct "falls" to read --flows--.

line 51, Correct "long" to read --along--.

Column 5, line 4, Change "outer" to read --other--.

*Signed and Sealed this*

*Twenty-first* Day of *November 1978*

[SEAL]

*Attest:*

RUTH C. MASON
*Attesting Officer*

DONALD W. BANNER
*Commissioner of Patents and Trademarks*